US012781191B2

(12) United States Patent
Fioret et al.

(10) Patent No.: US 12,781,191 B2
(45) Date of Patent: Nov. 3, 2026

(54) METHODS AND COMPOSITIONS FOR IMPROVING ENDOTHELIAL CELL BARRIER

(71) Applicant: United Therapeutics Corporation, Silver Spring, MD (US)

(72) Inventors: Bryan Fioret, Durham, NC (US); Thomas Petersen, Durham, NC (US); Ryan Bonvillain, Cary, NC (US); David Graham, Hillsborough, NC (US); Peter Vu, Raleigh, NC (US); Lotte van den Goor, Ypsilanti, MI (US)

(73) Assignee: United Therapeutics Corporation, Silver Spring, MD (US)

( * ) Notice: Subject to any disclaimer, the term of this patent is extended or adjusted under 35 U.S.C. 154(b) by 914 days.

(21) Appl. No.: 18/077,038

(22) Filed: Dec. 7, 2022

(65) Prior Publication Data

US 2023/0174947 A1 Jun. 8, 2023

Related U.S. Application Data

(60) Provisional application No. 63/399,494, filed on Aug. 19, 2022, provisional application No. 63/287,254, filed on Dec. 8, 2021.

(51) Int. Cl.
*C12N 5/071* (2010.01)

(52) U.S. Cl.
CPC .......... *C12N 5/069* (2013.01); *C12N 2500/33* (2013.01); *C12N 2500/36* (2013.01)

(58) Field of Classification Search
None
See application file for complete search history.

(56) References Cited

U.S. PATENT DOCUMENTS 10,731,135 B2 8/2020 Ren et al.
2020/0182861 A1 6/2020 Christensen

OTHER PUBLICATIONS

Akhtar et al., "RAC1 Regulates Adherens Junctions through Endocytosis of E-Cadherin," Molecular Biology of the Cell, Apr. 1, 2001, 12(4):847-862.
Birukova et al., "Rae GTPase is a hub for protein kinase A and Epac signaling in endothelial barrier protection by cAMP," Microvascular Research, Mar. 1, 2010, 79(2):128-138.
Butler et al., "Functional characterization of sphingosine 1-phosphate receptor agonist in human endothelial cells," Prostaglandins & Other Lipid Mediators, 2004, 73(1-2):29-45.
Kim et al., "Fingolimod and related compounds in a spontaneous autoimmune polyneuropathy," Journal of Neuroimmunology, Sep. 29, 2009, 214(1-2):93-100.
Poirier et al., "A G protein-biased S1P 1 agonist, SAR247799, protects endothelial cells without affecting lymphocyte numbers," Science Signaling, Jun. 2, 2020, 13(634):eaax8050, 14 pages.
Ren et al., "Engineering pulmonary vasculature in decellularized rat and human lungs," Nature Biotechnology, Sep. 14, 2015, 33(10):1097-1102.
Scott et al., "Ozanimod (RPC1063) is a potent sphingosine-1-phosphate receptor-1 (S1P1) and receptor-5 (S1P5) agonist with autoimmune disease-modifying activity," British Journal of Pharmacology, Apr. 28, 2016, 173(11):1778-1792.
Vandenbroucke et al., "Regulation of Endothelial Junctional Permeability," Annals of the New York Academy of Sciences, Mar. 19, 2008, 1123(1):134-145.
Garcia et al., "Sphingosine 1-phosphate promotes endothelial cell barrier integrity by Edg-dependent cytoskeletal rearrangement," The Journal of Clinical Investigation, Sep. 2001, 108(5):689-701.

*Primary Examiner* — Teresa E Knight
(74) *Attorney, Agent, or Firm* — Foley & Lardner LLP

(57) ABSTRACT

Described herein are methods and compositions for use in improving a vascular barrier of endothelial cells. The methods may include the use of barrier agonist compounds and improved techniques for culturing endothelial cells. The improved methods and compositions for culturing endothelial cells may include at least one or more of the following: an adenylyl cyclase activator; an activator of Sphingosine-1-phosphate (S1P) receptor internalization; a direct or indirect inducer of tight junction protein expression, and a direct or indirect inducer of adherens junction protein expression.

4 Claims, 10 Drawing Sheets

HPAEC culture in MCDB131
normalized impedence
time post treatment
15 hours
48 hours
5 days (120hrs)

HPAEC culture in HPLM
MCDB131 complete, untreated
HPLM complete, untreated
Treated with Forskolin and FTY720P Untreated (MCDB131 only)
Treated (MCDB131 +Forskolin & FTY720P)

FITC-Dextran (ug/mL)
0
10
20
30
40
*
20 minutes

FITC-Dextran (ug/mL)
0
20
40
60
80
*
40 minutes

FITC-Dextran (ug/mL)
0
50
100
150
**
120 minutes

TJ – tight junction
AJ – adherens junction

FF = Forskolin + FTY720P
MP = methylprednisolone

METHODS AND COMPOSITIONS FOR IMPROVING ENDOTHELIAL CELL BARRIER

CROSS-REFERENCE TO RELATED APPLICATIONS

This application claims priority to U.S. Provisional Application No. 63/287,254, filed Dec. 8, 2021, and U.S. Provisional Application No. 63/399,494, filed Aug. 19, 2022, the entire contents of which are incorporated herein by reference.

TECHNICAL FIELD

This application relates generally to cell culture and more particularly, but without limitation, to methods and compositions for improving a vascular barrier of endothelial cells, as well as cells produced from such methods.

BACKGROUND

The present application relates to the use of barrier agonist compounds to enhance the vascular barrier of endothelial cells in culture.

Lung tissue engineering is a promising but challenging field with the potential to supply healthy, transplantable lungs to the more than 400,000 Americans who die of lung disease every year. One strategy to generate tissue-engineered transplantable lungs is via a decellularization-recellularization method using a porcine lung as a starting scaffold. One of the greatest challenges to successful transplant of such a lung scaffold is restoring a mature, functional vascular barrier. A critical component of a mature vascular barrier is endothelial expression of tight and adherens junctional proteins, which help to regulate passage of fluid and molecules from the bloodstream to the underlying lung tissue.

Preventing leak from the recellularized vasculature of the porcine lung scaffold remains a significant challenge. One reason that recellularized lung scaffolds fail during functional testing (e.g., in ex vivo lung perfusion) is flooding of the airways due to vascular leak. Thus, there exists an unmet need for methods and compositions that reduce cell vascular leak in cultured endothelial cells.

SUMMARY

The present disclosure addresses drawbacks of previously-known approaches by providing methods and compositions for producing endothelial cells with an enhanced vascular barrier. The methods and compositions of the present disclosure may be used to produce cultured endothelial cells with an enhanced vascular barrier characterized by reduced vascular leak. Also provided herein are improved methods and compositions for the production of lung tissue from endothelial cells with an enhanced vascular barrier.

A method of producing endothelial cells may include contacting the endothelial cells with at least two barrier agonist compounds. In some embodiments, a method of producing endothelial cells may further include contacting the endothelial cells with at least two barrier agonist compounds during culturing. In numerous embodiments, contacting endothelial cells with at least two barrier agonist compounds may be performed for a period of time sufficient to permit strengthening of the vascular barrier of the endothelial cells. In some aspects, strengthening of the vascular barrier is determined by a reduction in vascular leak.

Endothelial cells of the present disclosure may be any human or non-human endothelial cells. Endothelial cells of the present disclosure may be lung endothelial cells. In some embodiments, endothelial cells may be selected from the group consisting of human pulmonary artery endothelial cells (HPAECs) and human lung microvascular endothelial cells (HMVECs). In some aspects, a method of producing endothelial cells further includes producing a transplantable lung with the endothelial cells.

Barrier agonist compounds of the present disclosure may include one or more compounds that promote increased expression of endothelial cell-cell junctions, that promote increased production of cyclic adenosine monophosphate, that promote increased production of adherens junction proteins (e.g., VE-Cadherin), or that promote increased production of tight junction proteins (e.g., ZO-1, JAM-A, Claudin-5, Occludin). In some preferred embodiments, a method of producing endothelial cells may include contacting the endothelial cells with at least two barrier agonist compounds, wherein the at least two barrier agonist compounds include forskolin and fingolimod-phosphate. In some embodiments, the barrier agonist compounds may further include methylprednisolone. In some such embodiments of a method of producing endothelial cells, forskolin may be present at a concentration of about 30 μM to about 50 μM. Preferably, forskolin may be present at a concentration of about 40 μM. In some embodiments, fingolimod-phosphate may be present at a concentration of about 5 nM to about 50 nM. Preferably, fingolimod-phosphate may be present at a concentration of about 50 nM. In some preferred embodiments, forskolin may be present at a concentration of about 40 μM, and fingolimod-phosphate may be present at a concentration of about 50 nM.

Disclosed herein are improved methods for producing lung tissue from cultured endothelial cells in a cell culture medium. In some embodiments, the improvements include (i) contacting the cultured endothelial cells with at least two barrier agonist compounds; and (ii) maintaining the endothelial cells in the cell culture medium for a period of time sufficient to permit strengthening of a vascular barrier of the endothelial cells, wherein strengthening of the vascular barrier is characterized by a reduction in vascular leak. In some embodiments, the at least two barrier agonist compounds may include forskolin and fingolimod-phosphate. In some such embodiments of an improved method of producing lung tissue from cultured endothelial cells in a cell culture medium, forskolin may be present at a concentration of about 30 μM to about 50 μM. Preferably, forskolin may be present at a concentration of about 40 μM. In some embodiments, fingolimod-phosphate may be present at a concentration of about 5 nM to about 50 nM. Preferably, fingolimod-phosphate may be present at a concentration of about 50 nM. In some preferred embodiments of such an improved method, forskolin may be present at a concentration of about 40 μM, and fingolimod-phosphate may be present at a concentration of about 50 nM.

The present disclosure provides cell culture medium compositions useful for producing endothelial cells. A cell culture medium composition may include at least two barrier agonist compounds. In some embodiments, the at least two barrier agonist compounds included in a cell culture medium composition of the present disclosure may include forskolin and fingolimod-phosphate. In some embodiments, the barrier agonist compounds included in a cell culture medium composition of the present disclosure may include forskolin, fingolimod-phosphate, and methylprednisolone.

Both the foregoing summary and the following description of the drawings and detailed description are exemplary and explanatory. They are intended to provide further details of the disclosure, but are not to be construed as limiting. Other objects, advantages, and novel features will be readily apparent to those skilled in the art from the following detailed description of the disclosure.

BRIEF DESCRIPTION OF THE DRAWINGS

(FIG. 2A) Normalized impedance as measured by ECIS in various treatment conditions. (FIG. 2B) Raw ECIS traces obtained in various treatment conditions.

(FIG. 3A) Normalized impedance as measured by ECIS in various treatment conditions. (FIG. 3B) Raw ECIS traces obtained in various treatment conditions.

(FIG. 4A) Normalized impedance as measured by ECIS in various treatment conditions. (FIG. 4B) Raw ECIS traces obtained in various treatment conditions.

(FIG. 7A) Percentage of cells positive for each assayed junction protein. (FIG. 7B) Raw traces.

(FIG. 10A) Shown is a quantification of cell number over time, under various treatment conditions. Cells were treated with medium alone or medium plus barrier agonist compounds at 0 hours post-seeding. (FIG. 10B) Shown is a quantification of cell number over time, under various treatment conditions. Cells were treated with medium alone or medium plus barrier agonist compounds at 48 hours post-seeding. Two-way ANOVA with multiple comparisons was performed; p<0.001.

DETAILED DESCRIPTION

Figures 1A, 1B:
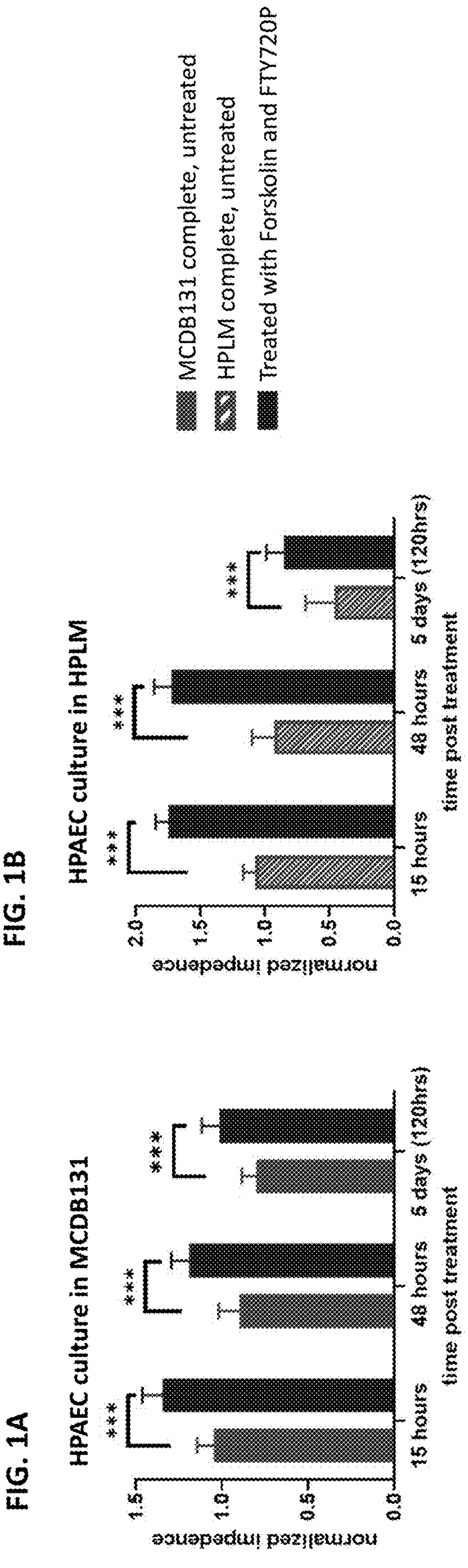
FIGS. 1A and 1B illustrate the efficacy of barrier agonist compounds forskolin and FTY720P in increasing the impedance of cultured HPAECs 15 hours, 48 hours, and 120 hours following treatment in (FIG. 1A) MCDB131 culture medium and (FIG. 1B) HPLM culture medium.

Embodiments according to the present disclosure will be described more fully hereinafter. Aspects of the disclosure may, however, be embodied in different forms and should not be construed as limited to the embodiments set forth herein. Rather, these embodiments are provided so that this disclosure will be thorough and complete, and will fully convey the scope of the invention to those skilled in the art. The terminology used in the description herein is for the purpose of describing particular embodiments only and is not intended to be limiting.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. Although not explicitly defined below, such terms should be interpreted according to their common meaning.

The terminology used in the description herein is for the purpose of describing particular embodiments only and is not intended to be limiting of the invention. All publications, patent applications, patents and other references mentioned herein are incorporated by reference in their entirety. In case of conflict, the present specification, including definitions, will control. Other aspects are set forth within the claims that follow.

The practice of the present technology will employ, unless otherwise indicated, conventional techniques of tissue culture, immunology, molecular biology, microbiology, chemical engineering, and cell biology, which are within the skill of the art.

Unless the context indicates otherwise, it is specifically intended that the various features described herein can be used in any combination. Moreover, the disclosure also contemplates that in some embodiments, any feature or combination of features set forth herein can be excluded or omitted. To illustrate, if the specification states that a complex comprises components A, B, and C (or A, B, and/or C), it is specifically intended that any of A, B or C, or a combination thereof, can be omitted and disclaimed singularly or in any combination.

Unless explicitly indicated otherwise, all specified embodiments, features, and terms intend to include both the recited embodiment, feature, or term and biological equivalents thereof.

All numerical designations, e.g., pH, temperature, time, concentration, and molecular weight, including ranges, are approximations that can be varied (+) or (−) by increments of 1.0 or 0.1, as appropriate, or alternatively by a variation of +/−15%, or alternatively 10%, or alternatively 5%, or alternatively 2%. It is to be understood, although not always explicitly stated, that all numerical designations are preceded by the term "about".

Definitions

As used in the description of the invention and the appended claims, the singular forms "a," "an" and "the" are intended to include the plural forms as well, unless the context clearly indicates otherwise.

The terms "substantially" and "about" are used herein to describe and account for small variations. When used in conjunction with an event or circumstance, the terms can refer to instances in which the event or circumstance occurs precisely as well as instances in which the event or circumstance occurs to a close approximation. When used in conjunction with a numerical value, the terms can refer to a range of variation of less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. When referring to a first numerical value as "substantially" or "about" the same as a second numerical value, the terms can refer to the first numerical value being within a range of variation of less than or equal to ±10% of the second numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. The terms or "acceptable," "effective," or "sufficient" when used to describe the selection of any components, ranges, dose forms, etc. disclosed herein intend that said component, range, dose form, etc. is suitable for the disclosed purpose.

Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

Also as used herein, "and/or" refers to and encompasses any and all possible combinations of one or more of the associated listed items, as well as the lack of combinations when interpreted in the alternative ("or").

As used herein, "optional" or "optionally" means that the subsequently described event or circumstance can or cannot occur, and that the description includes instances where the event or circumstance occurs and instances where it does not.

As used herein, the term "barrier agonist compound" refers to any compound that can enhance a vascular barrier of endothelial cells, as determined by, for example, a reduction in vascular leak. Barrier agonist compounds may enhance a vascular barrier of endothelial cells through one or more overlapping or distinct mechanisms. As a non-limiting example, generally, barrier agonists may enhance the endothelial expression of tight and adherens junctional proteins, which help to regulate passage of fluid and molecules from the bloodstream to the underlying lung tissue.

As used herein, the term "complete media" and "complete medium" refers to a cell culture media that are optimized for enhancing the vascular barrier of endothelial cells (e.g., Human Pulmonary Artery Endothelial Cells (HPAECs), Human Microvascular Endothelial Cells (HMVECs)). In some instances, a complete medium comprises inorganic salts, trace elements, vitamins, amino acids, lipids, carbohydrates, cytokines, growth factors, small molecules, and/or additional proteins, in which the ratio of the components to one another has been optimized for enhancement of a vascular barrier. In some embodiments, a complete medium comprises 1× large vessel endothelial supplement (LVES). In some embodiments, a complete medium comprises EGF, Hydrocortisone, Ascorbic Acid, Heparan Sulfate, FGF basic, about 2% FBS, about 2 ng/mL VEGF, and about 30 nM Sodium Selenite. Exemplary additional proteins include albumin, transferrin, fibronectin, and insulin. Exemplary carbohydrates include glucose. Exemplary inorganic salts include sodium, potassium, and calcium ions. Exemplary trace elements include zinc, copper, selenium, and tricarboxylic acid. Exemplary amino acids include essential amino acids such as L-glutamine (e.g., alanyl-1-glutamine or glycyl-1-glutamine); or non-essential amino acids (NEAA) such as glycine, L-alanine, L-asparagine, L-aspartic acid, L-glutamic acid, L-proline, and/or L-serine. Exemplary small molecules include forskolin, fingolimod-phosphate (FTY720P), and methylprednisolone (MP). In some embodiments, the complete media also comprises one or more of sodium bicarbonate ($NaHCO_3$), HEPES (4-(2-hydroxyethyl)-1-piperazine ethanesulfonic acid), phenol red, antibiotics, and/or β-mercaptoethanol. In some instances, the complete medium is a serum-free media. In some instances, the complete media is a xeno-free media.

As used herein, the term "endothelial cell" refers to any cell of the endothelium. In general, endothelial cells form a single cell layer that lines all blood vessels and regulates exchanges between the bloodstream and the surrounding tissues (Alberts B, Johnson A, Lewis J, et al., Molecular Biology of the Cell. $4^{th}$ Edition. Garland Science; 2002). An endothelial cell may be an endothelial cell of any organ system. For example, an endothelial cell may be a lung endothelial cell or a pulmonary endothelial cell. An endothelial cell may be a human or non-human endothelial cell. An endothelial cell may be a cultured endothelial cell. Endothelial cells may be isolated from organ tissue using any method known in the art. Endothelial cells may be cultured using any method known in the art.

As used herein, the term "vascular leak" refers to the movement of fluid across a vascular barrier or membrane. In some embodiments, vascular leak refers to the extravasation of fluids and molecules from inside blood vessels into underlying tissues. In some embodiments, an increase in vascular leak reflects an increase in the permeability of an endothelial cell barrier, and a decrease in vascular leak reflects a decrease in the permeability of an endothelial cell barrier.

Compositions for Improving Endothelial Cell Barrier

A cell culture media composition for enhancing a vascular barrier of endothelial cells is also provided herein. In some embodiments, a cell culture media composition for enhancing a vascular barrier of cultured endothelial cells is provided.

In some aspects, a cell culture media composition for enhancing a vascular barrier of endothelial cells comprises at least one barrier agonist compound. In some embodiments, a cell culture media composition for enhancing a vascular barrier of endothelial cells comprises at least two (i.e., 2, 3, 4, 5, or more) barrier agonist compounds. Non-limiting examples of barrier agonist compounds include: adenylyl cyclase activators; activators of Sphingosine-1-phosphate (S1P) receptor internalization; direct or indirect activators of the signaling enzyme Rac1; direct or indirect inducers of tight junction protein (e.g., ZO-1, JAM-A, Claudin-5, and Occludin) expression, and direct or indirect inducers of adherens junction protein (e.g., VE-Cadherin) expression. In some instances, a cell culture medium is an FBS-based media, optionally supplemented with at least one barrier agonist compound. In some instances, a cell culture medium is a serum-free media, optionally supplemented with one or more barrier agonist compounds. In some instances, a cell culture medium is a minimum media, optionally supplemented with one or more barrier agonist compounds. In some instances, a cell culture medium further comprises one or more amino acid supplements (e.g., L-glutamine) and/or antibiotics. In some cases, a cell culture medium composition is used with a method described infra for enhancing a vascular barrier of endothelial cells, such as, for example, lung endothelial cells, Human Pulmonary Artery Endothelial Cells (HPAECs), or Human Microvascular Endothelial Cells (HMVECs).

In some embodiments endothelial cells are lung endothelial cells. In some embodiments endothelial cells are pulmonary endothelial cells. In some embodiments endothelial cells are human endothelial cells. In some embodiments, endothelial cells are cultured endothelial cells. In some embodiments, endothelial cells are Human Pulmonary Artery Endothelial Cells (HPAECs) or Human Microvascular Endothelial Cells (HMVECs).

In some embodiments of a cell culture media composition, an adenylyl cyclase activator may be present at a concentration from about 1 μM to about 100 μM in molar concentration, or any value or subrange there between. In some embodiments, an adenylyl cyclase activator may be present at a concentration from about 10 μM to about 60 μM in molar concentration, or any value or subrange there between. In some embodiments, an adenylyl cyclase activator may be present at a concentration from about 30 μM to about 50 μM in molar concentration, or any value or subrange there between. For product concentrations, an adenylyl cyclase activator further may be included at a molar concentration of about, 30 μM, 31 μM, 32 μM, 33 μM, 34 μM, 35 μM, 36 μM, 37 μM, 38 μM, 39 μM, 40 μM, 41 μM, 42 μM, 43 μM, 44 μM, 45 μM, 46 μM, 47 μM, 48 μM, 49 μM, or 50 μM. In some preferred embodiments, an adenylyl cyclase activator is included at a molar concentration of about 40 μM. In some embodiments, an adenylyl cyclase activator encompasses any activator that enhances the activity of adenylyl cyclase, or that increases the production of cyclic adenosine monophosphate (cAMP). In some embodiments, an adenylyl cyclase activator induces activation of the proteins Epac and Rap1, and/or Protein Kinase A (PKA), thereby inducing rearrangement of the plasma-membrane-adjacent actin cytoskeleton. In some embodiments, an adenylyl cyclase activator increases expression of an adherens junction protein (e.g., VE-Cadherin). In some instances, one or more adenylyl cyclase activators are included in the cell culture media composition. Non-limiting examples of direct and indirect activators of adenylyl cyclase include forskolin, cholera toxin, prostaglandin E1, Norepinephrine (NE), prostaglandin E2, prostaglandin 12, Pituitary Adenylate Cyclase-Activating Polypeptide 1-27 (PACAP 1-27), PACAP 1-38, and NKH 477.

In some embodiments of a cell culture media composition, an activator of S1P receptor internalization may be present at a concentration from about 1 nM to about 100 nM in molar concentration, or any value or subrange there between. In some embodiments, an activator of S1P receptor internalization may be present at a concentration from about 10 nM to about 70 nM in molar concentration, or any value or subrange there between. In some embodiments, an activator of S1P receptor internalization may be present at a concentration from about 40 nM to about 60 nM in molar concentration, or any value or subrange there between. For product concentrations, an activator of S1P receptor internalization further may be included at a molar concentration of about 40 nM, 41 nM, 42 nM, 43 nM, 44 nM, 45 nM, 46 nM, 47 nM, 48 nM, 49 nM, 50 nM, 51 nM, 52 nM, 53 nM, 54 nM, 55 nM, 56 nM, 57 nM, 58 nM, 59 nM, or 60 nM. In some preferred embodiments, an activator of S1P receptor internalization is included at a molar concentration of about 50 nM. In some embodiments, an activator of S1P receptor internalization encompasses any activator that increases the internalization of the S1P receptor. In some embodiments, an activator of S1P receptor internalization increases expression of tight junction proteins (e.g., ZO-1, JAM-A, Claudin-5, Occludin). In some instances, one or more activators of S1P receptor internalizations are included in the cell culture media composition. In some aspects, the activator of S1P receptor internalization may be fingolimod-phosphate (FTY720P) or S1P.

In some embodiments, a cell culture medium composition comprises at least one adenylyl cyclase activator and at least one activator of S1P receptor internalization. In some embodiments, a cell culture medium composition comprising at least one adenylyl cyclase activator and at least one activator of S1P receptor internalization comprises an adenylyl cyclase activator at a concentration in a range from about 1 μM to about 100 μM, and an activator of S1P receptor internalization at a concentration in a range from about 1 nM to about 100 nM. In some preferred embodiments, a cell culture medium composition comprising at least one adenylyl cyclase activator and at least one activator of S1P receptor internalization comprises an adenylyl cyclase activator at a concentration in a range from about 30 μM to about 50 μM, and an activator of S1P receptor internalization at a concentration in a range from about 40 nM to about 60 nM. In some preferred embodiments, a cell culture medium composition comprising at least one adenylyl cyclase activator and at least one activator of S1P receptor internalization comprises an adenylyl cyclase activator at a concentration of about 40 μM, and an activator of S1P receptor internalization at a concentration of about 50 nM.

In some embodiments, a cell culture medium composition comprises at least one adenylyl cyclase activator, at least one activator of S1P receptor internalization, and at least one additional barrier agonist compound. An additional barrier agonist compound may act through a mechanism that is substantially the same as or is distinct from those of the at least one adenylyl cyclase activator and the at least one activator of S1P receptor internalization. For example, an additional barrier agonist compound can be, without limitation, a compound that induces expression of endothelial adhesion molecules and/or influences transcriptional regulation of junctional proteins. In some embodiments, a cell culture medium composition comprises an adenylyl cyclase activator at a concentration in a range from about 1 μM to about 100 μM, an activator of S1P receptor internalization at a concentration in a range from about 1 nM to about 100 nM, and at least one additional barrier agonist compound at a concentration in a range from about 0.5 μM to about 50 μM. In some preferred embodiments, a cell culture medium composition comprises an adenylyl cyclase activator at a concentration in a range from about 30 μM to about 50 μM, an activator of S1P receptor internalization at a concentration in a range from about 40 nM to about 60 nM, and at least one additional barrier agonist compound at a concentration in a range from about 0.5 μM to about 2 μM. In some preferred embodiments, a cell culture medium composition comprises an adenylyl cyclase activator at a concentration of about 40 μM, and an activator of S1P receptor internalization at a concentration of about 50 nM, and at least one additional barrier agonist compound at a concentration of about 1 μM. In some embodiments, a cell culture medium composition comprises forskolin and FTY-720P. In some embodiments, the at least one additional barrier agonist compound is methylprednisolone. In some embodiments, a cell culture medium composition comprises forskolin, FTY-720P, and methylprednisolone.

In some embodiments of a culture media composition, the fetal bovine serum (FBS) may be from about 1% to about 10% volume concentration (v/v), or any value or subrange there between. For certain product concentrations, the fetal bovine serum may be included at a volume concentration (v/v) of about 1.25%, 1.5%, 1.75%, 2.0%, 2.25%, 2.5%, 2.75%, 3.0%, 3.25%, 3.5%, 3.75%, 4.0%, 4.25%, 4.5%, 4.75%, 5.0%, 5.25%, 5.5%, 5.75%, 6.0%, 6.25%, 6.5%, 6.75%, 7.0%, 7.25%, 7.5%, 7.75%, 8.0%, 8.25%, 8.5%, 8.75%, 9.0%, 9.25%, 9.5%, 9.75%, or 10.0%. In some instances, FBS is included at a concentration of about 2%.

In some embodiments of a culture media composition, the composition comprises a basal medium which is further supplemented with one or more additional components such as an adenylyl cyclase activator and an activator of S1P receptor internalization. In some instances, a basal medium is MCDB131 (Gibco (10372019)) medium. In some instances, a basal medium is HPLM (Gibco (A4899101)) medium. In some embodiments, a basal medium is Endothelial Cell Growth Media 2 (EGM2, PromoCell). In some instances, a culture medium composition comprises L-glutamine (e.g., GlutaMAX™). In some cases, a medium composition comprises from about 0.1 μg/mL to about 10,000 μg/mL. In some cases, a medium composition comprises from about 0.1 μg/mL to about 10,000 μg/mL. In some cases, a media composition comprises from about 0.1 μg/mL to about 100 μg/mL of an antibiotic. In some embodiments, a media composition comprises from about 0.1 μg/mL to about 50 μg/mL of an antibiotic. Non-limiting examples of antibiotics include Penicillin, Streptomycin, Amphotericin, Gentamicin, and Amphotericin B.

In some embodiments, the media composition comprises a basal medium selected from MCDB131 medium and HPLM medium. In some cases, the media composition further comprises EGF, Hydrocortisone, Ascorbic Acid, Heparan Sulfate, FGF basic, about 2% FBS, about 2 ng/mL VEGF, about 30 nM Sodium Selenite, forskolin, and FTY720P. In some cases, the media composition further comprises EGF, Hydrocortisone, Ascorbic Acid, Heparan Sulfate, FGF basic, about 2% FBS, about 2 ng/mL VEGF, about 30 nM Sodium Selenite, forskolin, FTY720P, and methylprednisolone (MP).

Methods for Improving Endothelial Cell Barrier

Disclosed herein, in certain embodiments, is a method for enhancing a vascular barrier of endothelial cells, including, for example, HPAECs and HMVECs.

One method to minimalize vascular leak is through increased expression of endothelial cell-cell junctional proteins. Endothelial cell-cell junctional proteins include, without limitation, tight junction (e.g., ZO-1, JAM-A, Claudin-5, Occludin) and adherens junction (e.g., VE-Cadherin) proteins. Previous methods for endothelial culture, particularly those for endothelial cell culture in or on a recellularized scaffold, involved growth in the microvascular endothelial cell culture medium MCDB131, which is not specifically designed to strengthen endothelial barrier. In these methods, the MCDB131 base media is combined with a large vessel endothelial supplement (LVES) to produce MCDB complete media, designed to prioritize cell proliferation over the formation of a stable vascular barrier (see Table 1).

TABLE 1

| Complete Media Components | MCDB131 | HPLM |
|---|---|---|
| Basal medium | Gibco (10372019) | Gibco (A4899101) |
| EGF | yes | yes |
| Hydrocortisone | yes | yes |
| Ascorbic Acid | yes | yes |
| Heparan Sulfate | yes | yes |
| FGF basic | yes | yes |
| FBS | 93 mL/L (~2%) | 93 mL/L (~2%) |
| VEGF | 2 ng/mL | 2 ng/mL |
| Sodium Selenite | 30 nM | 30 nM |

Provided herein are methods for producing endothelial cells in which strengthening of the vascular barrier is prioritized over cell proliferation. Prioritization of strengthening of a vascular barrier may be achieved through supplementation of a cell culture medium (e.g., MCDB131 or HPLM) with barrier agonist compounds (e.g., forskolin, fingolimod-phosphate (FTY720P), and/or methylprednisolone (MP)).

The signaling enzyme Rac1 serves as a critical intermediate in the vascular barrier strengthening process. Forskolin-induced increases in cAMP trigger Rac1 mediated endothelial barrier tightening. Forskolin stimulates the enzyme adenylyl cyclase to generate cyclic adenosine monophosphate (cAMP). cAMP utilizes two primary downstream signaling pathways to strengthen vascular barrier. cAMP binds directly to Epac1, which acts via Rap1 to stimulate guanine nucleotide exchange factors (GEFs) and activate Rac1. Alternatively, cAMP can activate PKA, which also leads to activation of Rac1 via GEFs. Rac1 activation, via Epac1/Rap1 or PKA, enhances the vascular barrier by strengthening the cortical actin cytoskeleton through the increased expression of tight and adherens junctional proteins (e.g. Claudin, Occludin, VE-Cadherin, etc.) (Schegel and Washke, Cell Tissue Res, 2014).

FTY720P, the phosphorylated and active metabolite of FTY720, induces internalization of the Sphingosine-1-phosphate (S1P) receptor, which moves from the plasma membrane into the cell cytoplasm, triggering further cytoskeletal rearrangement and barrier strengthening, in part from increased expression of Claudin-5. In addition, S1P (as well as FTY720P) also leads to activation of Rac1 and subsequent vascular barrier tightening.

Methylprednisolone (MP) is a synthetic anti-inflammatory glucocorticoid. Direct gene targets of this glucocorticoid include tight junctions (Occludins, Claudin-5) and adherens junctions (VE-Cadherin). MP is also an anti-edematous agent with a role in fluid reabsorption, inducing upregulation of aquaporin water channels to increase cell membrane permeability to water. MP acts by binding to the glucocorticoid receptor (GR) in the cell cytoplasm. The GC-GR complex translocates to the nucleus, where it stimulates transcription of junctional proteins via the GC-responsive element (GRE).

In some embodiments, the present disclosure provides methods for culturing endothelial cells with a strengthened vascular barrier. In some embodiments, cultured endothelial cells are lung endothelial cells. In some embodiments, cultured endothelial cells are pulmonary endothelial cells. In some embodiments, cultured endothelial cells are human endothelial cells. In some embodiments, cultured endothelial cells are Human Pulmonary Artery Endothelial Cells (HPAECs) or Human Microvascular Endothelial Cells (HMVECs). Endothelial cells may be cultured by method known in the art. Endothelial cells may be cultured on a two-dimensional substrate or a three-dimensional substrate.

HPAECs are cells originating from human pulmonary artery endothelium. They are adherent and have a cobblestone appearance. HPAECs may be characterized by expression of surface protein markers platelet endothelial cell adhesion molecule (PECAM/CD31) and vascular endothelial cadherin (VE-cadherin/CD144). They also express von Willebrand Factor (vWF), vascular endothelial growth factor receptor 2 (VEGFR-2/Flk-1/KDR), vascular endothelial growth factor 1 (VEGFR1/Flt-1), and endothelial nitric oxide synthase (eNOS). Functional attributes of HPAECs in vitro include uptake of acetylated low density lipoproteins (Ac-LDLs) and tube formation.

In some embodiments, the present disclosure provides methods for producing endothelial cells. In some embodiments, the present disclosure provides methods for producing endothelial cells with an enhanced vascular barrier. In some embodiments, the present disclosure provides a method for producing endothelial cells comprising contacting the endothelial cells with at least two barrier agonist compounds. In some embodiments, the present disclosure provides a method for producing endothelial cells comprising contacting the endothelial cells with at least three barrier agonist compounds. In some aspects, such a method comprises culturing endothelial cells in a cell culture medium, wherein contacting the endothelial cells with at least two barrier agonist compounds is performed during culturing. Generally, endothelial cells may be contacted by barrier agonist compounds when the endothelial cells are confluent in culture. In some embodiments, endothelial cells may be contacted by barrier agonist compounds when the endothelial cells are about 50%, about 60%, about 70%, about 75%, about 80%, about 85%, about 90%, about 95%, about 96%, about 97%, about 98%, about 99%, or about 100% confluent in culture.

In some embodiments, the present disclosure provides a method for producing endothelial cells comprising contacting the endothelial cells with at least one barrier agonist compound. In some aspects, such a method comprises culturing endothelial cells in a cell culture medium, wherein contacting the endothelial cells with at least one barrier agonist compound is performed during culturing. Generally, endothelial cells may be contacted by a barrier agonist compound when the endothelial cells are confluent in culture. In some embodiments, endothelial cells may be contacted by a barrier agonist compound when the endothelial cells are about 50%, about 60%, about 70%, about 75%, about 80%, about 85%, about 90%, about 95%, about 96%, about 97%, about 98%, about 99%, or about 100% confluent in culture.

In some embodiments, barrier agonist compounds may be directly added to a cell culture medium comprising endothelial cells. In some aspects, endothelial cells may be contacted with a barrier agonist compound by adding the barrier agonist compound directly to the cell culture medium in which the endothelial cells are cultured. In some instances, endothelial cells may be contacted with a barrier agonist compound by contacting the endothelial cells with a cell culture medium comprising the barrier agonist compound.

In some embodiments, endothelial cells may be contacted with at least one barrier agonist compound for a period of time sufficient to permit strengthening of the vascular barrier of the endothelial cells. In some embodiments, a period of time sufficient to permit strengthening of the vascular barrier of the endothelial cells may be in a range from about 1 hour to about 10 days. In some embodiments, a period of time sufficient to permit strengthening of the vascular barrier of the endothelial cells may be at least 1 hour, at least 2 hours, at least 10 hours, at least 15 hours, at least 24 hours, at least 36 hours, at least 48 hours, at least 72 hours, at least 96 hours, at least 100 hours, at least 120 hours, or at least 150 or more hours. In some embodiments, endothelial cells may undergo one or more cycles of media replacement. In some embodiments, endothelial cells may not undergo any cycles of media replacement. For example, and for illustrative purposes only, endothelial cells contacted with a barrier agonist compound for 120 hours may be maintained in the same culture medium comprising a barrier agonist compound for 120 hours without undergoing media replacement. As an alternative example, for illustrative purposes only, endothelial cells contacted with a barrier agonist compound for 120 hours may be subjected to one, two, three, or more cycles of media replacement over the course of the 120 hour period of contact, wherein each cycle of medium replacement comprises removing cultured medium from the cells, and supplying new medium to the cells, the new medium comprising a barrier agonist compound.

In some aspects, strengthening of a vascular barrier is determined and/or characterized by a reduction in vascular leak. In general, vascular leak is the movement of fluid and molecules across a vascular barrier, for example, from the bloodstream to underlying tissue. Vascular leak may be assayed by any applicable technique in accordance with the present disclosure. Non-limiting examples of techniques for measuring vascular leak or for quantifying vascular barrier tightening include electric cell-substrate impedance sensing (ECIS), transendothelial electrical resistance (TEER) measurement, and Fluorescein isothiocyanate (FITC)-dextran transendothelial permeability assays.

In some embodiments, the present disclosure provides methods for producing a transplantable organ with endothelial cells produced according to the methods described herein. Non-limiting examples of transplantable organs include lung, heart, kidney, and liver. In some embodiments, a transplantable organ is a transplantable lung.

Any type of endothelial cell may be used in accordance with the present disclosure. Non-limiting examples of endothelial cells include human pulmonary vein endothelial cell (HPVECs), human aortic endothelial cells (HAoECs), human coronary artery endothelial cells (HCAECs), human liver sinusoidal endothelial cell (HLSECs), human glomerular endothelial cell (HGECs), and human umbilical vein endothelial cells (HUVECs). In some embodiments, endothelial cells are selected from the group consisting of human pulmonary artery endothelial cells (HPAECs) and human lung microvascular endothelial cells (HMVECs).

In some embodiments of a method of producing endothelial cells, an adenylyl cyclase activator may be present at a concentration from about 1 μM to about 100 μM in molar concentration, or any value or subrange there between. In some aspects of a method of producing endothelial cells, an adenylyl cyclase activator may be present at a concentration from about 10 μM to about 60 μM in molar concentration, or any value or subrange there between. In some embodiments, an adenylyl cyclase activator may be present at a concentration from about 30 μM to about 50 μM in molar concentration, or any value or subrange there between. In some embodiments of a method of producing endothelial cells, an adenylyl cyclase activator further may be included at a molar concentration of about, 30 μM, 31 μM, 32 μM, 33 μM, 34 μM, 35 μM, 36 μM, 37 μM, 38 μM, 39 μM, 40 μM, 41 μM, 42 μM, 43 μM, 44 μM, 45 μM, 46 μM, 47 μM, 48 μM, 49 μM, or 50 μM. In some preferred embodiments, an adenylyl cyclase activator is included at a molar concentration of about 40 μM. In some embodiments, an adenylyl cyclase activator encompasses any activator that enhances the activity of adenylyl cyclase, or that increases the production of cyclic adenosine monophosphate (cAMP). In some embodiments, an adenylyl cyclase activator encompasses induces activation of the proteins Epac and Rap1, thereby inducing rearrangement of the cortical actin cytoskeleton. In some embodiments, an adenylyl cyclase activator increases expression of adherens junction proteins, such as VE-Cadherin. In some instances, one or more adenylyl cyclase activators are included in the cell culture media composition used in a method of producing endothelial cells. Non-limiting examples of direct and indirect activators of adenylyl cyclase include forskolin, cholera toxin, prostaglandin E1, Norepinephrine (NE), prostaglandin E2, prostaglandin 12, Pituitary Adenylate Cyclase-Activating Polypeptide 1-27 (PACAP 1-27), PACAP 1-38, and NKH 477.

In some embodiments of a method of producing endothelial cells, an activator of S1P receptor internalization may be present at a concentration from about 1 nM to about 100 nM in molar concentration, or any value or subrange there between. In some aspects, an activator of S1P receptor internalization may be present at a concentration from about 10 nM to about 70 nM in molar concentration, or any value or subrange there between. In some embodiments of a method of producing endothelial cells, an activator of S1P receptor internalization may be present at a concentration from about 40 nM to about 60 nM in molar concentration, or any value or subrange there between. In some embodiments of a method of producing endothelial cells, an activator of S1P receptor internalization may be included at a molar concentration of about 40 nM, 41 nM, 42 nM, 43 nM, 44 nM, 45 nM, 46 nM, 47 nM, 48 nM, 49 nM, 50 nM, 51 nM, 52 nM, 53 nM, 54 nM, 55 nM, 56 nM, 57 nM, 58 nM, 59 nM, or 60 nM. In some preferred embodiments, an activator of S1P receptor internalization is included at a molar concentration of about 50 nM. In some embodiments, an activator of S1P receptor internalization encompasses any activator that increases the internalization of the S1P receptor. In some embodiments, an activator of S1P receptor internalization increases expression of tight junction proteins (e.g., ZO-1, JAM-A, Claudin-5, and/or Occludin). In some instances, one or more activators of S1P receptor internalizations are included in the cell culture media composition used in a method of producing endothelial cells. In some aspects, an activator of S1P receptor internalization may be fingolimod-phosphate (FTY720P) or S1P.

In some embodiments of a method of producing endothelial cells, methylprednisolone (MP) may be present in culture medium at a concentration from about 0.1 μM to about 50 μM in molar concentration, or any value or subrange there between. In some aspects, methylprednisolone may be present at a concentration from about 0.5 μM to about 10 μM in molar concentration, or any value or subrange there between. In some aspects, methylprednisolone may be present at a concentration from about 0.5 μM to about 2 μM in molar concentration, or any value or subrange there between. In some embodiments of a method of producing endothelial cells, methylprednisolone may be included at a molar concentration of about 0.5 μM, about 0.6 μM, about 0.7 μM, about 0.8 μM, about 0.9 μM, about 1 μM, about 1.1 μM, about 1.2 μM, about 1.3 μM, about 1.4 μM, about 1.5 μM, about 1.6 μM, about 1.7 μM, about 1.8 μM, about 1.9 μM, or about 2 μM. In some preferred embodiments, methylprednisolone is included at a molar concentration of about 1 μM. In some embodiments, methylprednisolone increases vascular barrier integrity, such as by inducing expression of adhesion molecules.

In some embodiments, a method of producing endothelial cells comprises contacting the endothelial cells with at least two barrier agonist compounds. In some such embodiments, a method of producing endothelial cells comprises contacting the endothelial cells with at least one adenylyl cyclase activator and at least one activator of S1P receptor internalization. In some embodiments, a method of producing endothelial cells comprises contacting the endothelial cells with at least one adenylyl cyclase activator and at least one activator of S1P receptor internalization, wherein the at least one adenylyl cyclase activator is present at a concentration in a range from about 1 μM to about 100 μM, and the at least one activator of S1P receptor internalization is present at a concentration in a range from about 1 nM to about 100 nM. In some preferred embodiments, a method of producing endothelial cells comprises contacting the endothelial cells with at least one adenylyl cyclase activator and at least one activator of S1P receptor internalization, wherein the at least one adenylyl cyclase activator is present at a concentration in a range from about 30 μM to about 50 μM, and the at least one activator of S1P receptor internalization is present at a concentration in a range from about 40 nM to about 60 nM. In some preferred embodiments, a method of producing endothelial cells comprises contacting the endothelial cells with at least one adenylyl cyclase activator and at least one activator of S1P receptor internalization, wherein the at least one adenylyl cyclase activator is present at a concentration of about 40 μM, and the at least one activator of S1P receptor internalization is present at a concentration of about 50 nM.

In some embodiments, a method of producing endothelial cells comprises contacting the endothelial cells with at least three barrier agonist compounds. In some such embodiments, a method of producing endothelial cells comprises contacting the endothelial cells with at least one adenylyl cyclase activator and at least one activator of S1P receptor internalization. In some embodiments, a method of producing endothelial cells comprises contacting the endothelial cells with at least one adenylyl cyclase activator and at least one activator of S1P receptor internalization, wherein at least one adenylyl cyclase activator is present at a concentration in a range from about 1 μM to about 100 μM, and at least one activator of S1P receptor internalization is present at a concentration in a range from about 1 nM to about 100 nM. In some preferred embodiments, a method of producing endothelial cells comprises contacting the endothelial cells with at least one adenylyl cyclase activator and at least one activator of S1P receptor internalization, wherein at least one adenylyl cyclase activator is present at a concentration in a range from about 30 μM to about 50 μM, and at least one activator of S1P receptor internalization is present at a concentration in a range from about 40 nM to about 60 nM. In some preferred embodiments, a method of producing endothelial cells comprises contacting the endothelial cells with at least one adenylyl cyclase activator and at least one activator of S1P receptor internalization, wherein at least one adenylyl cyclase activator is present at a concentration of about 40 μM, and at least one activator of S1P receptor internalization is present at a concentration of about 50 nM. In some embodiments, a method of producing endothelial cells may include contacting the endothelial cells with at least three (i.e., 3, 4, 5, 6, or more) barrier agonist compounds, wherein the at least three barrier agonist compounds include forskolin, fingolimod-phosphate, and methylprednisolone (MP). In some such embodiments of a method of producing endothelial cells, forskolin may be present at a concentration of about 30 μM to about 50 μM. Preferably, forskolin may be present at a concentration of about 40 μM. In some embodiments, fingolimod-phosphate may be present at a concentration of about 5 nM to about 50 nM. Preferably, fingolimod-phosphate may be present at a concentration of about 50 nM. In some preferred embodiments, forskolin may be present at a concentration of about 40 μM, and fingolimod-phosphate may be present at a concentration of about 50 nM. In some embodiments, methylprednisolone may be present at a concentration of about 0.5 μM to about 2 μM. In some preferred embodiments, methylprednisolone may be present at a concentration of about 1 μM. In some preferred embodiments, forskolin may be present at a concentration of about 40 μM, fingolimod-phosphate may be present at a concentration of about 50 nM, and methylprednisolone may be present at a concentration of about 1 μM.

The present disclosure provides improvements to method of producing lung tissue from cultured endothelial cells in a cell culture medium. In some embodiments, improvements to a method of producing lung tissue from cultured endothelial cells in a cell culture medium includes steps of (i) contacting the cultured endothelial cells with at least one barrier agonist compound; and (ii) maintaining the endothelial cells in the cell culture medium for a period of time sufficient to permit strengthening of a vascular barrier of the endothelial cells, wherein strengthening of the vascular barrier is characterized by a reduction in vascular leak. In some embodiments, improvements to a method of producing lung tissue from cultured endothelial cells in a cell culture medium includes steps of (i) contacting the cultured endothelial cells with at least two barrier agonist compounds; and (ii) maintaining the endothelial cells in the cell culture medium for a period of time sufficient to permit strengthening of a vascular barrier of the endothelial cells, wherein strengthening of the vascular barrier is characterized by a reduction in vascular leak.

In some embodiments of a method of producing lung tissue from cultured endothelial cells in a cell culture medium, an adenylyl cyclase activator may be present at a concentration from about 1 μM to about 100 μM in molar concentration, or any value or subrange there between. In some aspects of a method of producing endothelial cells, an adenylyl cyclase activator may be present at a concentration from about 10 μM to about 60 μM in molar concentration, or any value or subrange there between. In some such embodiments, an adenylyl cyclase activator may be present at a concentration from about 30 μM to about 50 μM in molar concentration, or any value or subrange there between. In some embodiments of a method of producing lung tissue from cultured endothelial cells in a cell culture medium, an adenylyl cyclase activator further may be included at a molar concentration of about, 30 μM, 31 μM, 32 μM, 33 μM, 34 μM, 35 μM, 36 μM, 37 μM, 38 μM, 39 μM, 40 μM, 41 μM, 42 μM, 43 μM, 44 μM, 45 μM, 46 μM, 47 μM, 48 μM, 49 μM, or 50 μM. In some preferred embodiments, an adenylyl cyclase activator is included at a molar concentration of about 40 μM. In some embodiments, an adenylyl cyclase activator encompasses any activator that enhances the activity of adenylyl cyclase, or that increases the production of cyclic adenosine monophosphate (cAMP). In some embodiments, an adenylyl cyclase activator encompasses induces activation of the proteins Epac and Rap1 and/or PKA, thereby inducing rearrangement of the plasma-membrane-adjacent actin cytoskeleton. In some embodiments, an adenylyl cyclase activator increases expression of adherens junction proteins (e.g., VE-Cadherin). In some instances, one or more adenylyl cyclase activators are included in the cell culture media composition used in a method of producing lung tissue from cultured endothelial cells in a cell culture medium. Non-limiting examples of direct and indirect activators of adenylyl cyclase include forskolin, cholera toxin, prostaglandin E1, Norepinephrine (NE), prostaglandin E2, prostaglandin 12, Pituitary Adenylate Cyclase-Activating Polypeptide 1-27 (PACAP 1-27), PACAP 1-38, and NKH 477.

In some embodiments of a method of producing lung tissue from cultured endothelial cells in a cell culture medium, an activator of S1P receptor internalization may be present at a concentration from about 1 nM to about 100 nM in molar concentration, or any value or subrange there between. In some such embodiments, an activator of S1P receptor internalization may be present at a concentration from about 10 nM to about 70 nM in molar concentration, or any value or subrange there between. In some embodiments of a method of producing lung tissue from cultured endothelial cells in a cell culture medium, an activator of S1P receptor internalization may be present at a concentration from about 40 nM to about 60 nM in molar concentration, or any value or subrange there between. In some embodiments of a method of producing lung tissue from cultured endothelial cells in a cell culture medium, an activator of S1P receptor internalization may be included at a molar concentration of about 40 nM, 41 nM, 42 nM, 43 nM, 44 nM, 45 nM, 46 nM, 47 nM, 48 nM, 49 nM, 50 nM, 51 nM, 52 nM, 53 nM, 54 nM, 55 nM, 56 nM, 57 nM, 58 nM, 59 nM, or 60 nM. In some preferred embodiments, an activator of S1P receptor internalization is included at a molar concentration of about 50 nM. In some embodiments, an activator of S1P receptor internalization encompasses any activator that increases the internalization of the S1P receptor. In some embodiments, an activator of S1P receptor internalization increases expression of tight junction proteins (e.g., ZO-1, JAM-A, Claudin-5, and/or Occludin). In some instances, one or more activators of S1P receptor internalizations are included in the cell culture media composition used in a method of producing lung tissue from cultured endothelial cells in a cell culture medium. In some aspects, an activator of S1P receptor internalization may be fingolimod-phosphate (FTY720P) or S1P.

In some embodiments of a method of producing lung tissue from cultured endothelial cells in a cell culture medium, methylprednisolone (MP) may be present in culture medium at a concentration from about 0.1 μM to about 50 μM in molar concentration, or any value or subrange there between. In some aspects, methylprednisolone may be present at a concentration from about 0.5 μM to about 10 μM in molar concentration, or any value or subrange there between. In some aspects, methylprednisolone may be present at a concentration from about 0.5 μM to about 2 μM in molar concentration, or any value or subrange there between. In some embodiments of a method of producing endothelial cells, methylprednisolone may be included at a molar concentration of about 0.5 μM, about 0.6 μM, about 0.7 μM, about 0.8 μM, about 0.9 μM, about 1 μM, about 1.1 μM, about 1.2 μM, about 1.3 μM, about 1.4 μM, about 1.5 μM, about 1.6 μM, about 1.7 μM, about 1.8 μM, about 1.9 μM, or about 2 μM. In some preferred embodiments, methylprednisolone is included at a molar concentration of about 1 μM. In some embodiments, methylprednisolone increases vascular barrier integrity, such as by inducing expression of adhesion molecules.

In some embodiments, a method of producing lung tissue from cultured endothelial cells in a cell culture medium comprises contacting the endothelial cells with at least two barrier agonist compounds. In some such embodiments, a method of producing lung tissue from cultured endothelial cells in a cell culture medium comprises contacting the endothelial cells with at least one adenylyl cyclase activator and at least one activator of S1P receptor internalization. In some embodiments, a method of producing lung tissue from cultured endothelial cells in a cell culture medium comprises contacting the endothelial cells with at least one adenylyl cyclase activator and at least one activator of S1P receptor internalization, wherein the at least one adenylyl cyclase activator is present at a concentration in a range from about 1 μM to about 100 μM, and the at least one activator of S1P receptor internalization is present at a concentration in a range from about 1 nM to about 100 nM. In some preferred embodiments, a method of producing lung tissue from cultured endothelial cells in a cell culture medium comprises contacting the endothelial cells with at least one adenylyl cyclase activator and at least one activator of S1P receptor internalization, wherein the at least one adenylyl cyclase activator is present at a concentration in a range from about 30 μM to about 50 μM, and the at least one activator of S1P receptor internalization is present at a concentration in a range from about 40 nM to about 60 nM. In some preferred embodiments, a method of producing lung tissue from cultured endothelial cells in a cell culture medium comprises contacting the endothelial cells with at least one adenylyl cyclase activator and at least one activator of S1P receptor internalization, wherein the at least one adenylyl cyclase activator is present at a concentration of about 40 μM, and the at least one activator of S1P receptor internalization is present at a concentration of about 50 nM.

In some embodiments, a method of producing lung tissue from cultured endothelial cells in a cell culture medium comprises contacting the endothelial cells with at least three barrier agonist compounds. In some such embodiments, a method of producing lung tissue from cultured endothelial cells in a cell culture medium comprises contacting the endothelial cells with at least one adenylyl cyclase activator and at least one activator of S1P receptor internalization. In some embodiments, a method of producing lung tissue from cultured endothelial cells in a cell culture medium comprises contacting the endothelial cells with at least one adenylyl cyclase activator and at least one activator of S1P receptor internalization, wherein at least one adenylyl cyclase activator is present at a concentration in a range from about 1 μM to about 100 μM, and at least one activator of S1P receptor internalization is present at a concentration in a range from about 1 nM to about 100 nM. In some preferred embodiments, a method of producing lung tissue from cultured endothelial cells in a cell culture medium comprises contacting the endothelial cells with at least one adenylyl cyclase activator and at least one activator of S1P receptor internalization, wherein at least one adenylyl cyclase activator is present at a concentration in a range from about 30 μM to about 50 μM, and at least one activator of S1P receptor internalization is present at a concentration in a range from about 40 nM to about 60 nM. In some preferred embodiments, a method of producing lung tissue from cultured endothelial cells in a cell culture medium comprises contacting the endothelial cells with at least one adenylyl cyclase activator and at least one activator of S1P receptor internalization, wherein at least one adenylyl cyclase activator is present at a concentration of about 40 μM, and at least one activator of S1P receptor internalization is present at a concentration of about 50 nM. In some embodiments, a method of producing lung tissue from cultured endothelial cells in a cell culture medium may include contacting the endothelial cells with at least three (i.e., 3, 4, 5, 6, or more) barrier agonist compounds, wherein the at least three barrier agonist compounds include forskolin, fingolimod-phosphate, and methylprednisolone (MP). In some such embodiments of a method of producing lung tissue from cultured endothelial cells in a cell culture medium, forskolin may be present at a concentration of about 30 μM to about 50 μM. Preferably, forskolin may be present at a concentration of about 40 μM. In some embodiments, fingolimod-phosphate may be present at a concentration of about 5 nM to about 50 nM. Preferably, fingolimod-phosphate may be present at a concentration of about 50 nM. In some preferred embodiments, forskolin may be present at a concentration of about 40 μM, and fingolimod-phosphate may be present at a concentration of about 50 nM. In some embodiments, methylprednisolone may be present at a concentration of about 0.5 μM to about 2 μM. In some preferred embodiments, methylprednisolone may be present at a concentration of about 1 μM. In some preferred embodiments, forskolin may be present at a concentration of about 40 μM, fingolimod-phosphate may be present at a concentration of about 50 nM, and methylprednisolone may be present at a concentration of about 1 μM.

In some embodiments of a method of producing lung tissue from cultured endothelial cells in a cell culture medium, endothelial cells may be contacted with at least one barrier agonist compound for a period of time sufficient to permit strengthening of the vascular barrier of the endothelial cells. In some embodiments of a method of producing lung tissue from cultured endothelial cells in a cell culture medium, a period of time sufficient to permit strengthening of the vascular barrier of the endothelial cells may be in a range from about 1 hour to about 10 days. In some embodiments, a period of time sufficient to permit strengthening of the vascular barrier of the endothelial cells may be at least 1 hour, at least 2 hours, at least 10 hours, at least 15 hours, at least 24 hours, at least 36 hours, at least 48 hours, at least 72 hours, at least 96 hours, at least 100 hours, at least 120 hours, or at least 150 or more hours. In some such embodiments, endothelial cells may undergo one or more cycles of media replacement. In some embodiments, endothelial cells may not undergo any cycles of media replacement. For example, and for illustrative purposes only, in a method of producing lung tissue from cultured endothelial cells in a cell culture medium, endothelial cells contacted with a barrier agonist compound for 120 hours may be maintained in the same culture medium comprising a barrier agonist compound for 120 hours without undergoing media replacement. As an alternative example, for illustrative purposes only, in a method of producing lung tissue from cultured endothelial cells in a cell culture medium, endothelial cells contacted with a barrier agonist compound for 120 hours may be subjected to one, two, three, or more cycles of media replacement over the course of the 120 hour period of contact, wherein each cycle of medium replacement comprises removing cultured medium from the cells, and supplying new medium to the cells, the new medium comprising a barrier agonist compound.

EXAMPLES

These examples are provided for illustrative purposes only and not to limit the scope of the claims provided herein.

Example 1: Endothelial Cell Barrier Strengthening Compounds are Functional in Multiple Different Culture Media Culture Media Different cell culture media were tested to determine whether barrier agonist compounds can exert vascular barrier strengthening effects in multiple types of cell culture media. In one assay, two separate cell culture media were tested: 1) MCDB131 Complete Medium: MCDB131 base medium supplemented with 1× large vessel endothelial supplement (LVES) and 2) HPLM Complete Medium: Human plasma like media (HPLM) supplemented with 1×LVES. The components of each Complete medium are presented in Table 1.

Protocol

Human Pulmonary Artery Endothelial Cells (HPAECs) were cultured until confluent in either MCDB131 Complete or HPLM Complete media (where complete media contains 1×LVES, as defined in Table 1). Frozen vials of cells were thawed using a 37° C. water bath. Cells were seeded in a T75 flask at a cell density between 2,000-5,000 cells/cm$^2$ and cultured in complete medium (i.e., MCDB131 Complete or HPLM Complete). Cells were maintained in a 37° C., 20% 02, 5% $CO_2$ incubator. Cell growth was monitored, and media was replaced every 48 hours (i.e., days 3, 5, 7, etc. of culture).

Once confluent, the cells were treated with or without barrier agonists (forskolin, 40 μM and fingolimod-phosphate (FTY720P), 50 nM) and assayed for changes in barrier function using the xCELLigence platform (electrical cell-substrate impedance sensing (ECIS)) system. In brief, the xCELLigence-supported 96-well plate (ACEA Biosciences, E-Plate 96 PET, Cat. No. 00300600910) was prepared according to the manufacturer's protocol prior to seeding the plate with ~6,600 cells/well (corresponding to ~20,000 cells/mL). ECIS measurements were obtained at desired time points. Over the duration of the experiment, media was changed daily.

Electric cell-substrate impedance sensing (ECIS) results at 15 hours, 48 hours, and 5 days after barrier agonist treatment. Higher impedance values indicate a tighter endothelial barrier. All results were normalized to pretreatment impedance levels. Statistical analyses were performed using one-way ANOVA, Tukey multiple comparisons post-hoc test.

Results

As illustrated graphically in FIGS. 1A and 1B, the tested barrier agonist compounds were effective in enhancing the impedance of HPAECs cultured in (FIG. 1A) MCDB131 Complete medium and (FIG. 1B) HPLM Complete medium, at all time points tested. These data suggest that barrier agonist compounds are compatible with and effective in multiple different types of cell culture media.

Example 2: Optimization of Forskolin Concentration for Strengthening of the Vascular Barrier of Cultured Endothelial Cells In order to determine the concentration of forskolin that maximizes the observed endothelial cell barrier tightening effect, multiple concentrations of forskolin were tested in three separate experiments.

Experiment 1

Human Microvascular Endothelial Cells (HMVEC, from PromoCell, PC) were cultured until confluent in MCDB131 Complete medium as described in Example 1. Once confluent, cells were treated with forskolin (10 μM or 40 μM) or untreated (control). ECIS results were obtained at 15 hours, 48 hours, and 5 days (100 hours) after barrier agonist treatment.

Results

Figure 2A:
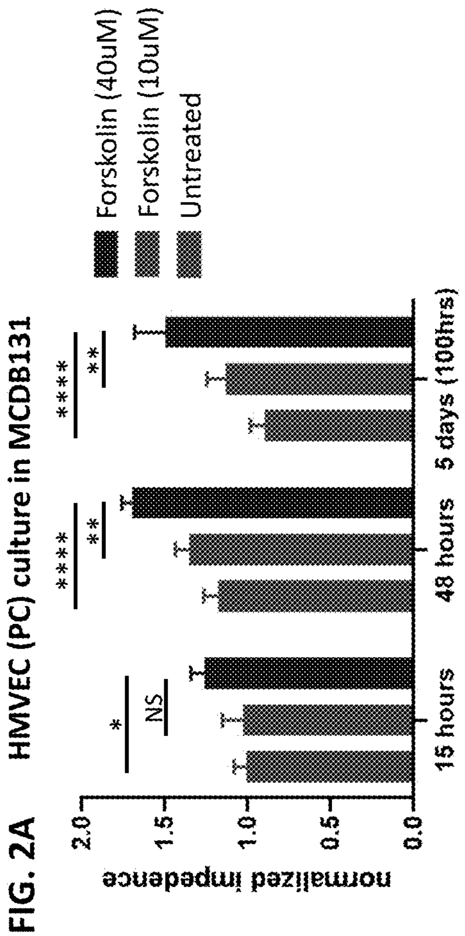
FIGS. 2A and 2B illustrate the efficacy of the barrier agonist compound forskolin in increasing the impedance of cultured HMVECs from PromoCell (PC) 15 hours, 48 hours, and 100 hours following treatment in MCDB131 culture medium with forskolin at 0 μM, 10 μM, or 40 μM.
Figure 2B:
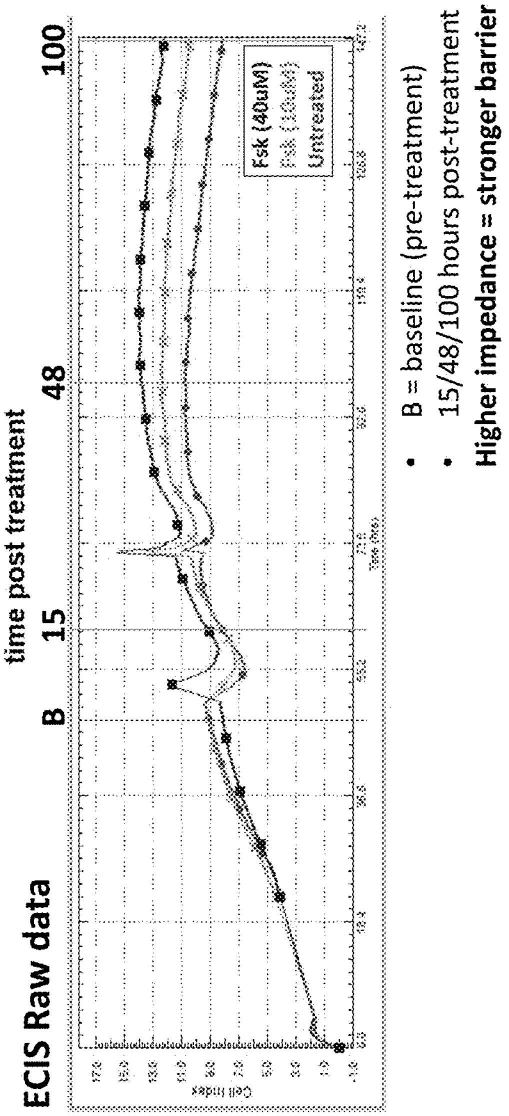

As illustrated graphically in FIGS. 2A and 2B, forskolin at 40 μM induced greater enhancement of vascular barrier strength than 10 μM forskolin or untreated control.

Experiment 2

Human Microvascular Endothelial Cells (HMVEC, from Cell Applications, CA) were cultured until confluent in MCDB131 Complete medium. Once confluent, cells were treated with forskolin (10 μM or 40 μM) or untreated (control). ECIS results were obtained at 15 hours, 48 hours, and 5 days (100 hours) after barrier agonist treatment.

Results

Figure 3A:
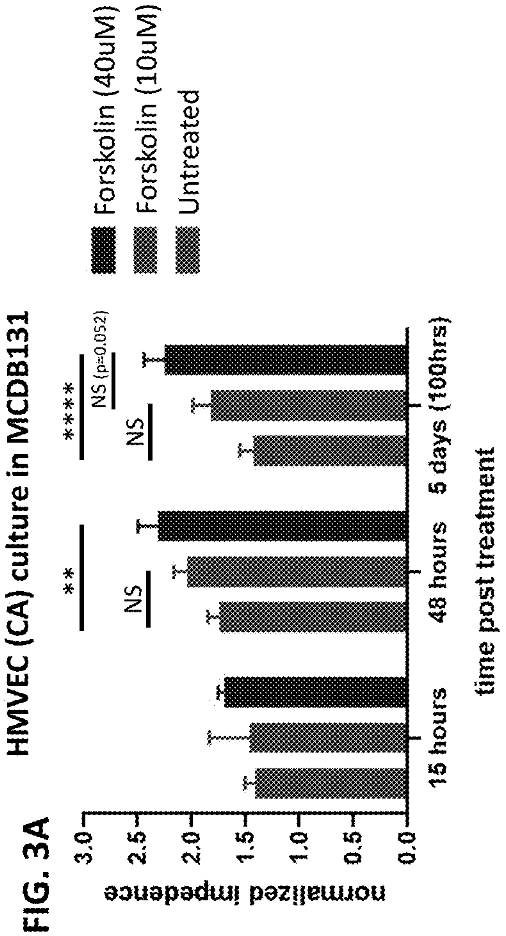
FIGS. 3A and 3B illustrates the efficacy of the barrier agonist compound forskolin in increasing the impedance of cultured HMVECs from Cell Applications (CA) 15 hours, 48 hours, and 100 hours following treatment in MCDB131 culture medium with forskolin at 0 μM, 10 μM, or 40 μM.
Figure 3B:
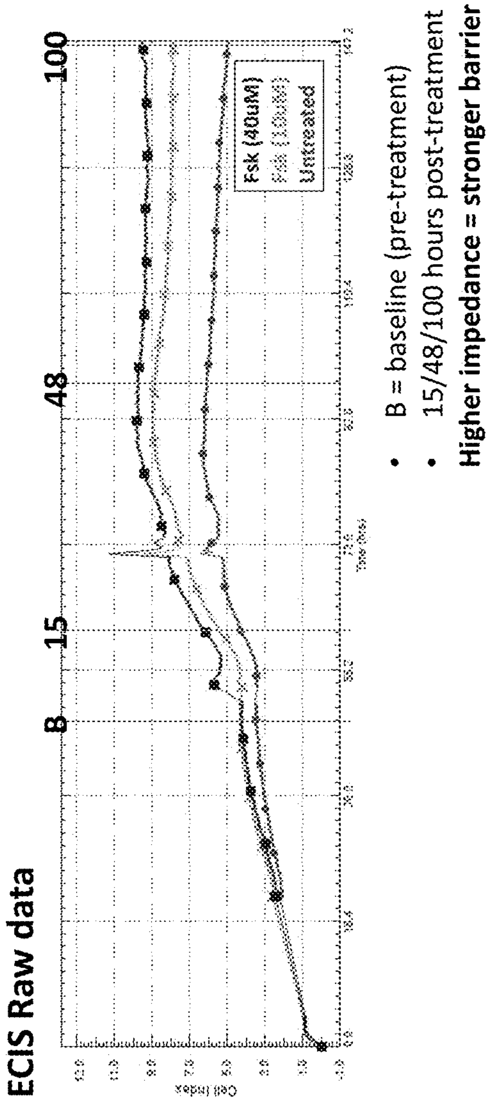

As illustrated graphically in FIGS. 3A and 3B, forskolin at 40 μM induced greater enhancement of vascular barrier strength then 10 μM forskolin or untreated control. These data, in view of the results of Experiment 1 of the present Example, and Example 1, demonstrate that forskolin exerts vascular barrier strengthening effects in multiple different types of endothelial cells.

Experiment 3

Human Pulmonary Artery Endothelial Cells (HPAECs, from ATCC) were cultured until confluent in MCDB131 Complete medium. Once confluent, cells were treated with forskolin (40 μM or 60 μM) or untreated (control). ECIS results were obtained at 15 hours, 48 hours, and 5 days (100 hours) after barrier agonist treatment.

Results

Figure 4A:
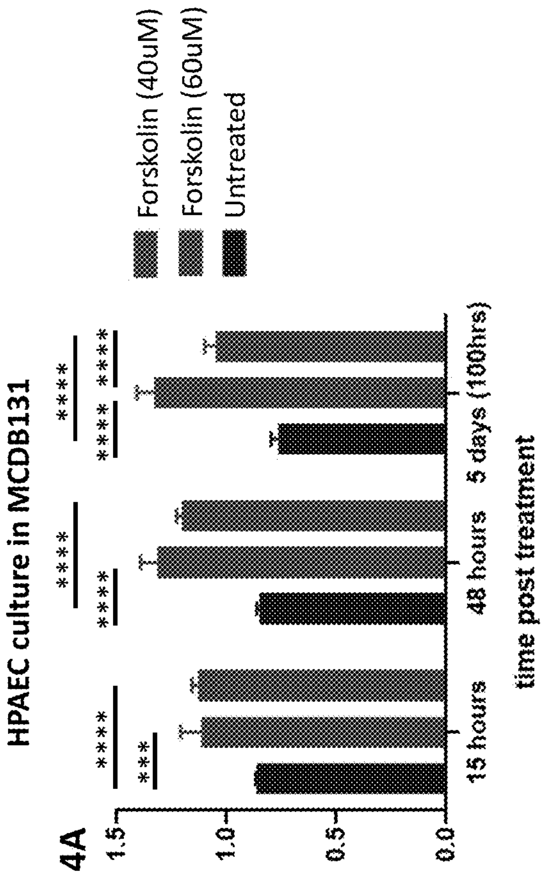
FIGS. 4A and 4B illustrate the efficacy of the barrier agonist compound forskolin in increasing the impedance of cultured HPAECs from ATCC 15 hours, 48 hours, and 100 hours following treatment in MCDB131 culture medium with forskolin at 0 μM, 40 μM, or 60 μM.
Figure 4B:
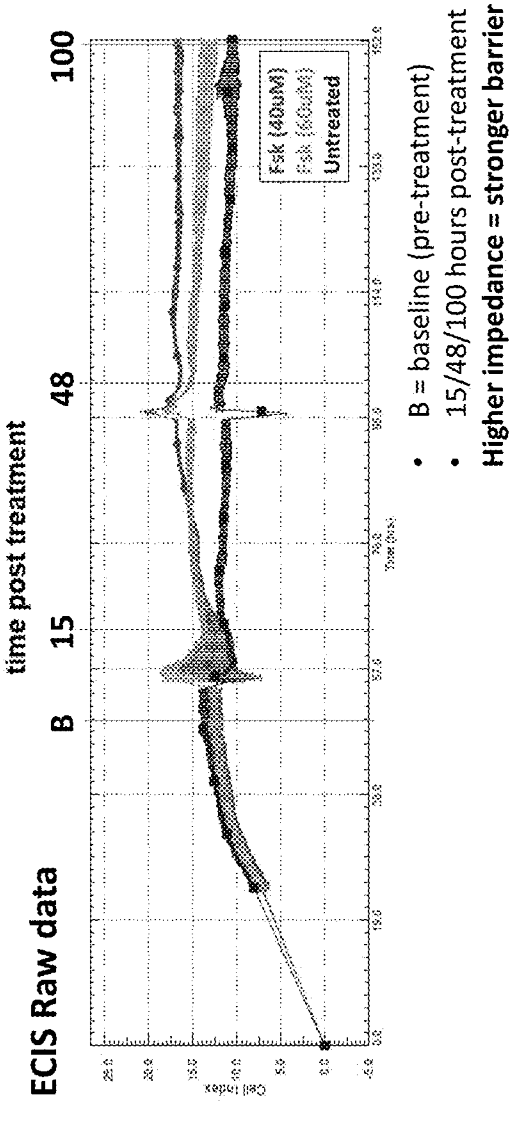

As illustrated graphically in FIGS. 4A and 4B, forskolin at 40 μM induced greater enhancement of vascular barrier strength than 60 μM forskolin or untreated control. These data demonstrate that forskolin exerts vascular barrier strengthening effects in multiple different types of endothelial cells, and that its vascular barrier strengthening effects occur optimally when forskolin is present at a concentration within a finite range.

Example 3: Optimization of FTY720P Concentration for Strengthening of the Vascular Barrier of Cultured Endothelial Cells In order to determine the concentration of FTY720P that maximizes the observed endothelial cell barrier tightening effect, multiple concentrations of FTY720P were tested.

Experiment 1

Human Pulmonary Artery Endothelial Cells (HPAECs, from ATCC) were cultured until confluent in MCDB131 Complete medium. Once confluent, cells were treated with forskolin (40 μM), forskolin (40 μM)+FTY720P (50 nM), forskolin (40 μM)+FTY720P (5 nM), or untreated (control). ECIS results were obtained at 15 hours, 48 hours, and 5 days (120 hours) after barrier agonist treatment.

Results

Figure 5:
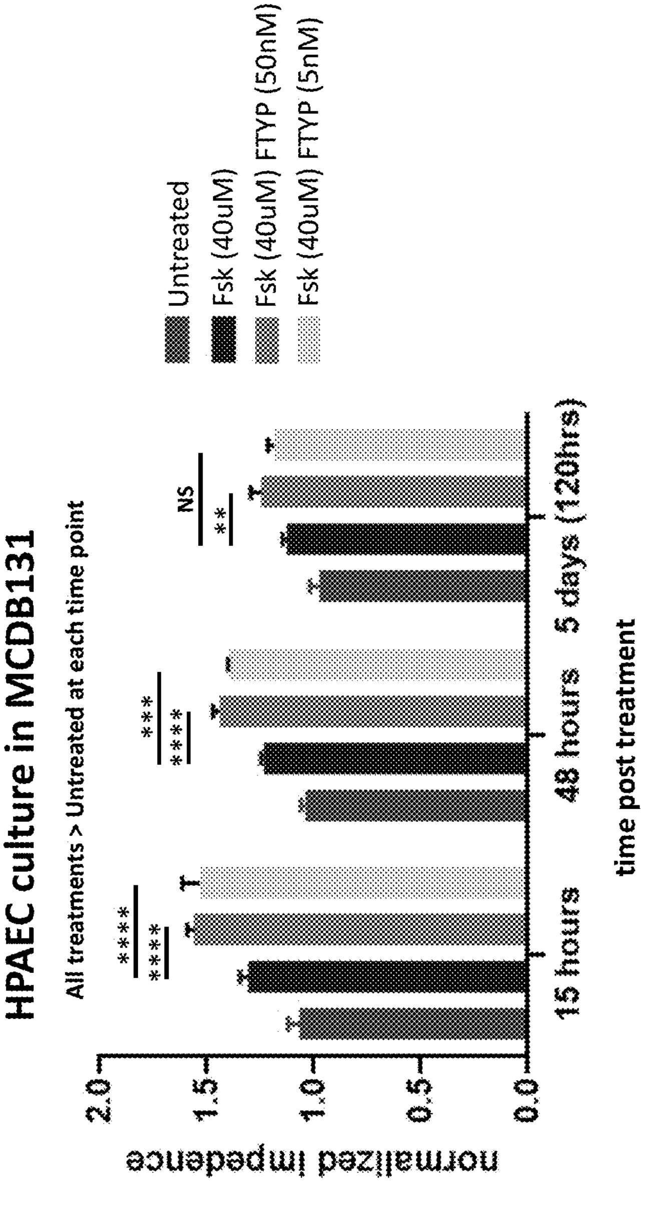
FIG. 5 illustrates the efficacy of the barrier agonist compounds forskolin and FTY720P in increasing the impedance of cultured HPAECs 15 hours, 48 hours, and 120 hours following treatment in MCDB131 culture medium with forskolin at 0 μM or 40 μM, and with FTY720P at 0 nM, 5 nM, or 50 nM.

As illustrated graphically in FIG. 5, forskolin (40 μM)+FTY720P (50 nM) induced greater enhancement of vascular barrier strength than forskolin (40 μM) alone, forskolin (40 μM)+FTY720P (5 nM), and untreated control. These data demonstrate that FTY720P (50 nM) can enhance the vascular barrier strengthening of endothelial cells when combined with forskolin, and that this effect is concentration-dependent.

Experiment 2

Human Pulmonary Artery Endothelial Cells (HPAECs) were cultured until confluent in MCDB131 Complete on a semi-permeable collagen-treated membrane. Once confluent, the cells were treated with or without barrier agonists (forskolin, 40 μM and fingolimod-phosphate (FTY720P), 50 nM) for 18 hours and assayed for changes in barrier function using the fluorescein isothiocyanate (FITC)-dextran transendothelial permeability assay. Following overnight (18 hour) incubation of cultured HPAECs in MCDB131 with or without barrier agonist compounds (as described above), cells were incubated in FITC-Dextran for 20, 40, or 120 minutes. Following incubation, levels of FITC-Dextran in the underlying medium (i.e., levels of FITC-Dextran having passed through the endothelial cell monolayer and underlying semi-permeable membrane) were quantified using a fluorescence plate reader with 485 nm excitation and 535 nm emission filters.

Results

Figures 6A, 6B, 6C:
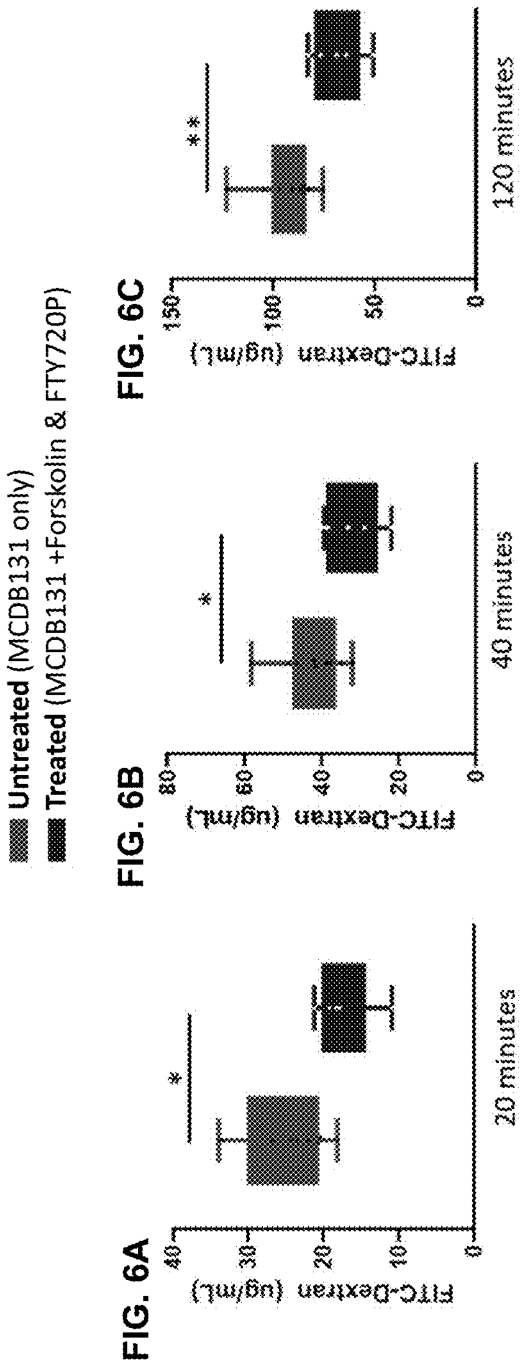
FIGS. 6A-6C illustrate the efficacy of the barrier agonist compounds forskolin and FTY720P in enhancing the vascular barrier of cultured HPAECs 18 hours following treatment in MCDB131 culture medium with forskolin (40 μM) and FTY720P (50 nM) as measured via the fluorescein isothiocyanate (FITC)-dextran transendothelial permeability assay.

As illustrated graphically in FIGS. 6A-6C, forskolin (40 μM)+FTY720P (50 nM) induced greater enhancement of vascular barrier strength (as measured by a decrease in the amount of FITC-Dextran passing through the endothelial cell monolayer and into the underlying medium) than that observed in the untreated control as measured after 20 minutes (FIG. 6A), 40 minutes (FIG. 6B), and 120 minutes (FIG. 6C) of incubation with FITC-Dextran. Small dots in each plot indicate individual wells tested. Statistical analysis performed using an unpaired t-test. These data provide orthogonal support to the ECIS-based findings in Example 3 Experiment 1, above.

Example 4: Forskolin and FTY720P Increase the Expression of Tight Junction and Adherens Junction Proteins at HPAEC Cell-Cell Junctions The present Example illustrates the efficacy of forskolin and FTY720P in enhancing the expression of tight junction and adherens junction proteins in cultured endothelial cells.

Protocol

Assessment by Flow Cytometry

Human Pulmonary Artery Endothelial Cells (HPAECs) were cultured until confluent in MCDB131 Complete media (where Complete media contains 1×LVES, as defined in Table 1). Once confluent, the cells were treated with or without barrier agonists (forskolin, M and fingolimod-phosphate (FTY720P), 50 nM) for 18 hours. Following treatment, HPAECs were fixed but not permeabilized, in order to preserve junctional proteins, and stained as indicated. Flow cytometry analysis was performed to quantify differences in expression of tight junction and adherens junction proteins.

Assessment by Immunofluorescence Staining

Human Pulmonary Artery Endothelial Cells (HPAECs) were cultured until confluent in MCDB131 Complete media (where Complete media contains 1×LVES, as defined in Table 1). Once confluent, the cells were treated with or without barrier agonists (forskolin, M and fingolimod-phosphate (FTY720P), 50 nM) for either 2 hours or 18 hours and assayed for changes in barrier function. Immunofluorescence staining of tight and adherens junctional markers (expressed on HPAECs) was performed using immunofluorescence-compatible antibodies.

Results

Figure 7A:
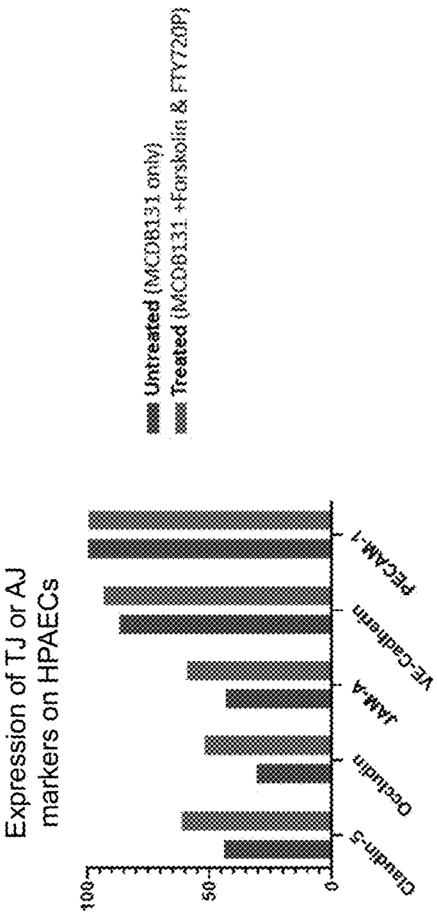
FIGS. 7A and 7B illustrate the efficacy of barrier agonist compounds forskolin and FTY720P in increasing the expression of tight junction (TJ) and adherens junction (AJ) proteins in cultured HPAECs 18 hours following treatment with both compounds as measured by flow cytometry.
Figure 7B:
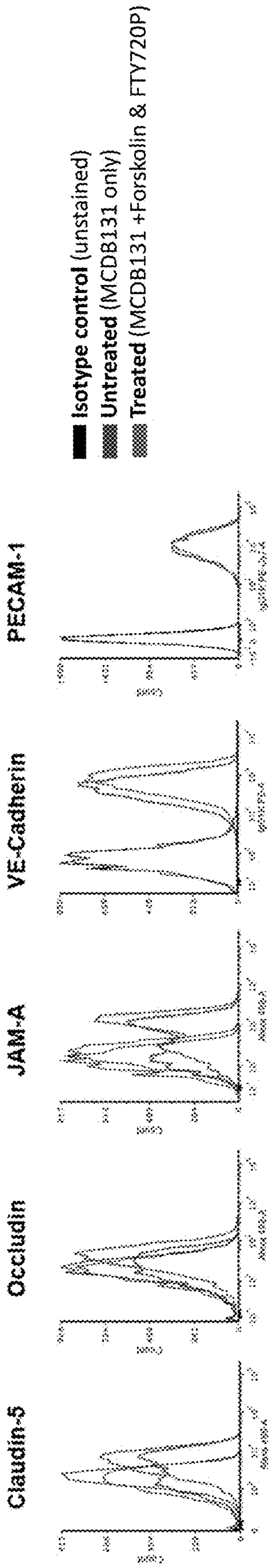

As illustrated graphically in FIGS. 7A and 7B, the tested barrier agonist compounds were effective in increasing the expression of tight junction and adherens junction proteins in cultured HPAECs as measured by flow cytometry. Quantification of cells positive for individual junctional markers using identical gating between treatment and control is summarized in FIG. 7A. The raw data are summarized in FIG. 7B. Rightward or upward shifts in the curve indicate greater presence of junctional proteins.

Figure 8B:
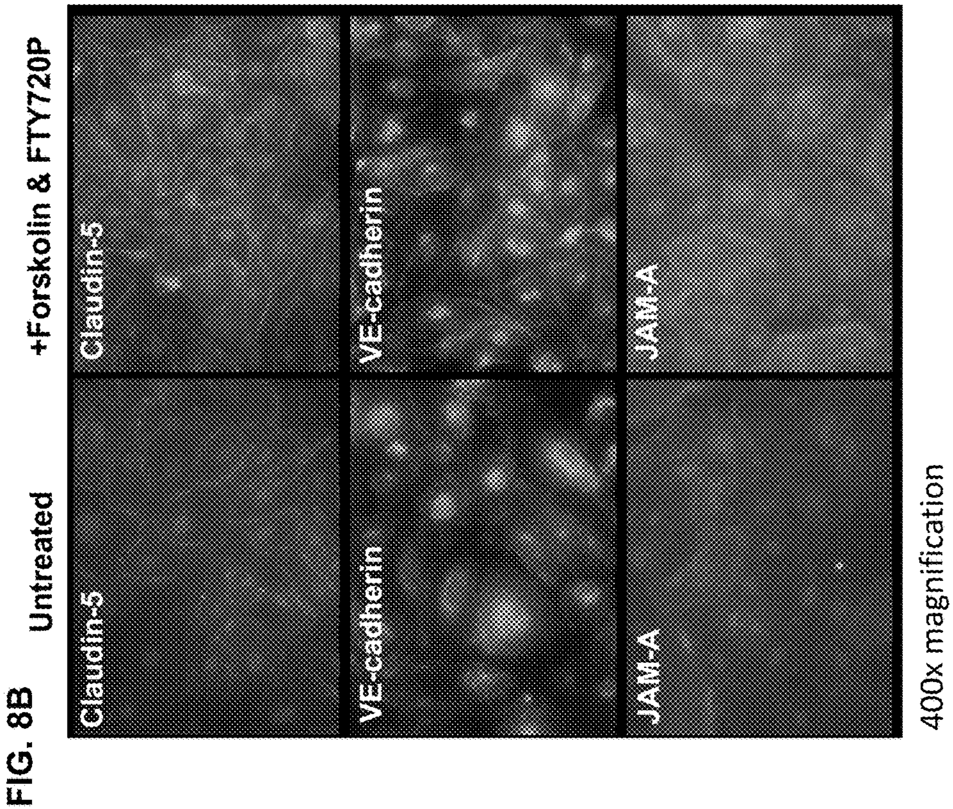
FIGS. 8A and 8B illustrate the efficacy of barrier agonist compounds forskolin and FTY720P in increasing the expression of tight junction and adherens junction proteins in the plasma membranes of cultured HPAECs (FIG. 8A) 2 hours and (FIG. 8B) 18 hours following treatment with both compounds as measured by immunofluorescence.
Figure 8A:
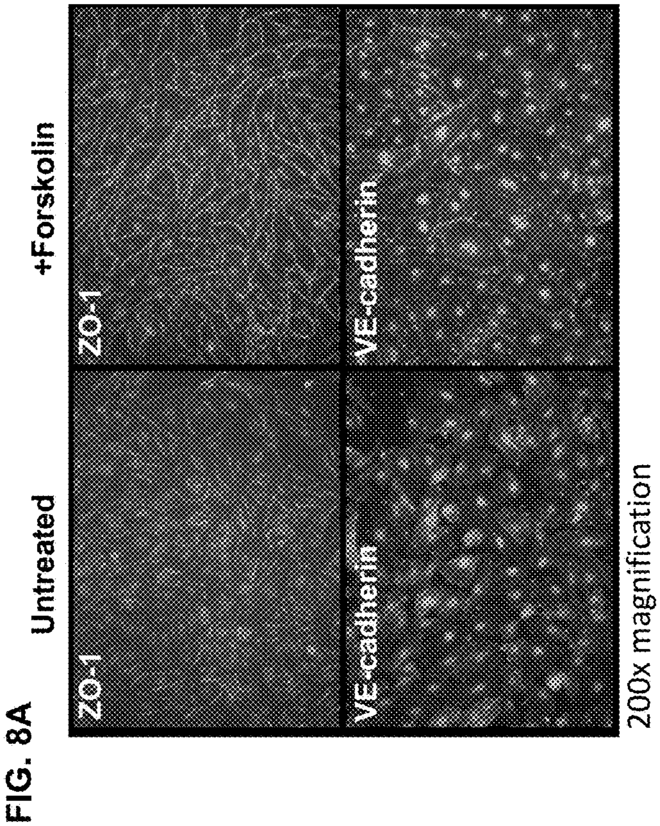

As illustrated in FIGS. 8A and 8B, the tested barrier agonist compounds (forskolin, 40 μM and fingolimod-phosphate (FTY720P), 50 nM) were effective in increasing the expression of tight junction (ZO-1, Claudin-5, and JAM-A) and adherens junction (VE-cadherin) proteins in the plasma membrane of cultured HPAECs as measured by immunofluorescence after 2 hours (FIG. 8A) and 18 hours (FIG. 8B) of treatment with the barrier agonist compounds.

Example 5: Forskolin, FTY720P, and Methylprednisolone Synergistically Increase the Transepithelial Electrical Resistance of Cultured HPAECs The present Example illustrates the synergistic effects of combining the barrier agonist compound methylprednisolone (MP) with Forskolin and Fingolimod phosphate to increase the transepithelial electrical resistance (TEER) of cultured HPAEC from ATCC.

Assessment of TEER

Barrier agonist treatment began on day 2 (48 hours) and was maintained through the remainder of culture. Cells were subjected to analysis of TEER using an EVOM™ Manual TEER measurement meter (EVOM 3 Instrument, Epithelial Volt/Ohm Meter) according to the manufacturer's protocol (EVOM™ Manual TEER Measurement Meter: Quick Start Guide, World Precision Instruments, which is incorporated herein by reference in its entirety). TEER measurements were acquired 24, 48, and 120 hours after barrier agonist treatment in MCDB131 culture medium. The barrier agonist compounds, when administered to the culture, were provided at the following concentrations: Forskolin (40 μM), FTY720-P (50 nM), Methylprednisolone (1 μM).

Results

Figure 9:
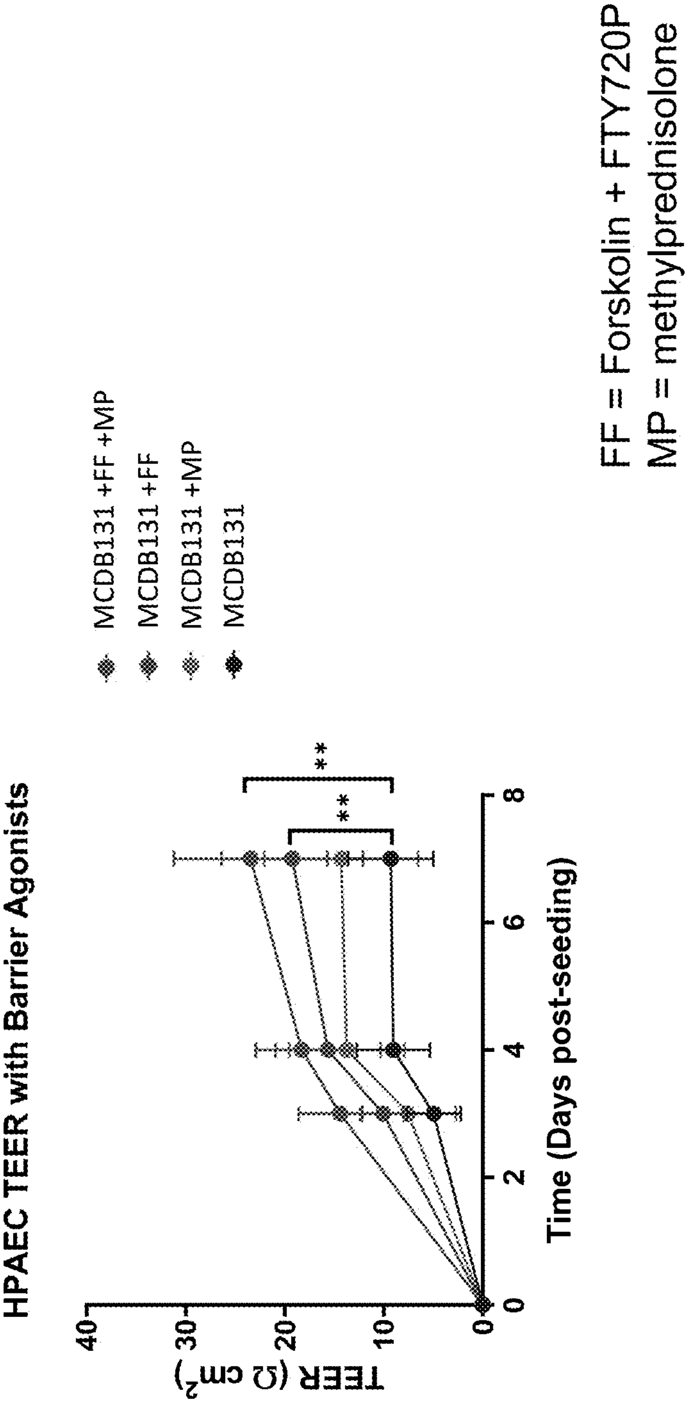
FIG. 9 illustrates the synergistic effects of combining the barrier agonist compound methylprednisolone (MP) with Forskolin and Fingolimod phosphate to increase the transepithelial electrical resistance (TEER) of cultured HPAEC. Two-way ANOVA with multiple comparisons was performed; **p<0.001 from N=3 separate biological replicates.

As shown in FIG. 9, methylprednisolone treatment resulted in a significant increase in TEER of cultured cells relative to cells cultured without any barrier agonist compound. While methylprednisolone alone did not increase TEER to a magnitude greater than that observed following treatment with Forskolin and FTY720-P, the combination of methylprednisolone, Forskolin, and FTY720-P resulted in a synergistic increased in TEER to a magnitude greater than that following treatment with Forskolin and FTY720-P.

Example 6: Barrier Agonist Compounds Regulate HPAEC Proliferation

The present Example illustrates the reduction in endothelial cell proliferation when cells are cultured in the presence of Forskolin (40 μM), and no reduction in endothelial proliferation when cultured with FTY720-P or MP.

Protocol

HPAECs were seeded at low initial confluency (3000-5000 cells/cm$^2$) to study their growth on Collagen type-I coated culture dishes. Barrier agonists were added at 0 hours (FIG. 10A) or at 48 hours (FIG. 10B) and were maintained through the remainder of culture. Barrier agonist compounds, when added to the culture medium (MCDB131), were added at the following concentrations: Forskolin (40 μM), FTY720-P (50 nM), Methylprednisolone (1 μM). Cell counts were measured through individual quantification of nuclei, stained with Hoechst dye and imaged on the Celigo Imaging Cytometer (Nexcelom Bioscience).

Results

Figure 10A:
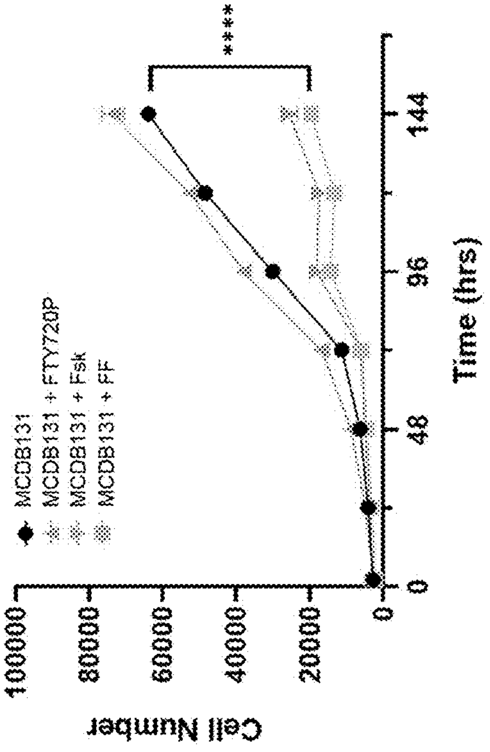
FIGS. 10A and 10B illustrate the effects of barrier agonist compounds on HPAEC proliferation in vitro.
Figure 10B:
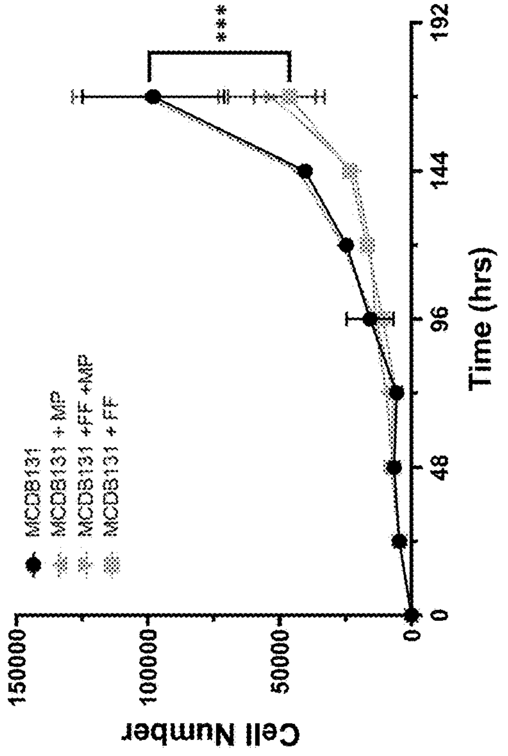

As shown in FIG. 10A, cells treated with Forskolin showed significantly lower endothelial cell proliferation than cells that were treated with FTY720-P or that received no treatment. As shown in FIG. 10B, cells treated with one or more barrier agonist compounds that include Forskolin exhibited significantly lower endothelial cell proliferation than groups without it (untreated or Methylprednisolone only).

These examples are provided for illustrative purposes only and not to limit the scope of the claims provided herein.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms “comprising,” “including,” “containing,” etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase “consisting essentially of” will be understood to include those elements specifically recited and those additional elements that do not materially affect the basic and novel characteristics of the claimed technology. The phrase “consisting of” excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, or compositions, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof, inclusive of the endpoints. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as “up to,” “at least,” “greater than,” “less than,” and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. In a method of producing lung tissue from cultured endothelial cells in a cell culture medium, the improvement that comprises:

(i) contacting the cultured endothelial cells with forskolin and fingolimod-phosphate; and (ii) maintaining the endothelial cells in the cell culture medium for a period of time sufficient to permit strengthening of a vascular barrier of the endothelial cells, wherein, following the step of contacting, the forskolin is present in the cell culture medium at a concentration of about 30 μM to about 50 μM, and the fingolimod-phosphate is present in the cell culture medium at a concentration of about 5 nM to about 50 nM, wherein strengthening of the vascular barrier is characterized by a reduction in vascular leak.

2. The method of claim 1, wherein, following the step of contacting, the forskolin is present in the cell culture medium at a concentration of about 40 μM.

3. The method of claim 1, wherein, following the step of contacting, the forskolin is present in the cell culture medium at a concentration of about 40 μM and the fingolimod-phosphate is present in the cells culture medium at a concentration of about 5 nM.

4. The method of claim 1, wherein, following the step of contacting, the forskolin is present in the cell culture medium at a concentration of about 40 μM, and the fingolimod-phosphate is present in the cell culture medium at a concentration of about 50 nM.

* * * * *